United States Patent [19]
Ajot et al.

[11] Patent Number: 5,239,482
[45] Date of Patent: Aug. 24, 1993

[54] METHOD OF AND AN APPARATUS FOR MEASURING THE ADSORPTION AND THE DESORPTION OF A GAS ADSORBED BY A SOLID SAMPLE AND THE USE THEREOF

[75] Inventors: Hubert Ajot, Rueil Malmaison; Jean F. Joly, Paris; Dominique A. Garnier, Argentan; Felix Marny, Aubergenville; Francis Raatz, Acheres; Colette Russmann, Eaubonne, all of France

[73] Assignee: Institut Francais du Petrole, Rueil Malmaison, France

[21] Appl. No.: 573,742

[22] Filed: Aug. 28, 1990

[30] Foreign Application Priority Data

Mar. 9, 1990 [FR] France ................... 90 05871

[51] Int. Cl.$^5$ .......................................... G01N 15/08
[52] U.S. Cl. .................................... 364/497; 73/38
[58] Field of Search ............ 73/38, 863.11; 364/497, 364/498

[56] References Cited

U.S. PATENT DOCUMENTS

| Re. 33,567 | 4/1991 | Killip et al. | 62/64 X |
|---|---|---|---|
| 3,707,870 | 1/1973 | Herve et al. | 73/38 |
| 3,850,040 | 11/1974 | Orr, Jr. et al. | 73/38 X |
| 4,487,213 | 12/1984 | Gates et al. | 137/487.5 X |
| 4,489,593 | 12/1984 | Pieters et al. | 73/865.5 X |
| 4,566,326 | 1/1986 | Lowell | 73/38 X |
| 4,693,124 | 9/1987 | Killip et al. | 62/64 X |
| 4,762,010 | 8/1988 | Borghard et al. | 73/38 X |
| 5,058,442 | 10/1991 | Yamanaka et al. | 73/38 X |
| 5,109,716 | 5/1992 | Ito et al. | 73/38 X |

OTHER PUBLICATIONS

J. E. Shields and S. Lowell, "A High Throughput Automated Instrument for Adsorption and Desorption Isotherms"; Jan./Feb. 1985, pp. 37, 40, 42, 44 and 46, International Laboratory.

Gregg et al., "The Physical Adsorption of Gases by Nonporous Solids: The Type II Isotherm," Adsorption, Surface Area and Porosity, 2nd edition, Academic Press, 1982, pp. 41-85.

Rouquerol et al., "A Critical Assessment of Quasi-Equilibrium Gas Techniques in Volumetry, Gravimetry or Calorimetry," Characterization of Porous Solids, Elsevier Science Publishers, 1988, pp. 67-76.

Primary Examiner—Edward R. Cosimano
Attorney, Agent, or Firm—Millen, White, Zelano, & Branigan

[57] ABSTRACT

For measuring the adsorption and desorption of a gas adsorbed by a solid sample, a gas pressure drop during the adsorption phase or a gas pressure increase during the desorption phase is programmed in the reservoir circuit 1 from 0.1 to 0.7 Pa per minute by at least one regulating valve $V_{P_1}$ having a proportional opening, in order to transfer a substantially constant flow of gas to the sample and from the sample to the reservoir, the gas pressure being measured periodically in the measuring circuit by pressure sensors. By a microprocessor, the isotherm of adsorption and desorption is determined based on the volume of the reservoir circuit, the quantity of gas transferred, the gas pressure in the measuring circuit, and the volume of the measuring circuit. The system measures the adsorption-desorption isotherms of a gas from a solid.

20 Claims, 2 Drawing Sheets

METHOD OF AND AN APPARATUS FOR MEASURING THE ADSORPTION AND THE DESORPTION OF A GAS ADSORBED BY A SOLID SAMPLE AND THE USE THEREOF

BACKGROUND OF THE INVENTION

The present invention relates to a method of and an apparatus for continuously measuring the adsorption-desorption isotherms of gases from solids. It also relates to the use of this apparatus particularly in a method of measuring the specific surface area of an adsorbent material.

Two major types of data may be extracted from the adsorption-desorption isotherms of gases from solids: First, in terms of physisorption, that is, at low temperatures, using molecules which do not give rise to specific interactions with particular surfaces sites (for example nitrogen argon or krypton at a temperature of 77° K.), the adsorption-desorption isotherms make it possible to characterize the textural properties of the solids. By processing some or all of these isotherms by well-known theories, e.g., BET, t, BJH, etc. (see, for example, "Adsorption, Surface Area and Porosity", S.J. Gregg and K.S.W. Sing, Academic Press Inc., second edition, 1982), one can determine such values as, for example, specific surface area, microporous volume, and porous distribution. Second, in terms of chemisorption, that is, at high temperatures, using molecules which give rise to a specific interaction with certain particular surface sites (for example ammonia carbon monoxide or hydrogen at temperatures in excess of 273° K.), it is possible to characterize the acidity or the metallic nature of the solids, i.e., the surface functions.

The textural properties and surface functions solids affects a variety of major industrial processes and fields such as, for example, catalysis, adsorption and cement production.

The adsorption-desorption isotherms of gas may be determined intermittently or continuously, the first technique being by far the more used. The intermittent technique consists, for adsorption, in injecting known doses of gas into an enclosure containing the previously pretreated solid. For desorption, the operation is reversed and the known quantities of gas are removed from the enclosure containing the sample. The two branches of the isotherm (adsorption-desorption) are thus described point by point. A plurality of commercial apparatuses which perform this type of procedure are available on the market and include, for example, equipment developed by Micromeritics and Erba Science.

Apparatus based on intermittent injection and extraction of known quantities of gas have a number of drawbacks. This type of procedure is not readily suited to the precise description of isotherms of type I in the low partial pressure range, because the volumes to be injected then become extremely small. On the other hand, the intermittent description of the isotherm does not make it possible to demonstrate the irregularities of minor amplitude which are presented by certain solids and which may reveal rearrangements of the adsorbed phase (see, for example, J. Rouquerol, F. Rouquerol, Y. Grillet and R.J. Ward in "Characterization of porous solids", Studies in Surface Science and Catalysis, Vol. 39 (1988), p. 67.

In principle, the intermittent adsorption or desorption technique is the best. It involves injecting (or withdrawing) the gas at constant and sufficiently low velocities that a thermodynamic equilibrium is constantly maintained. This technique has been proposed for a long time and has been perfected particularly by J. Rouquerol et al. French Patent Application No. 8810972, now French Patent 2,635,383), which demonstrates its feasibility. This technique, as it has been perfected recently, is, however, one which enjoys a limited range of application, a range which depends upon the natural pairing of adsorbate and temperature. For example, for nitrogen at 77° K. the limit partial pressure is around 0.4. This limitation is fairly simple to explain. To obtain low and constant rates of flow, conventional apparatuses employ a loss of head provided by a capillary to which a constant pressure is applied. The flow in such a system is more or less governed by Poiseuille's law which states that the rate of flow (Q) is proportional to the loss of head measured between the inlet to and outlet from the capillary. Therefore, the rate of flow is only approximately constant if the loss of head is itself constant. Well, when the pressure rises in the sample cell, the pressure upstream of the capillary being fixed and being generally less than 8 bars, the loss of head diminishes and consequently the rate of flow likewise diminishes. To ensure a constant rate of flow, one is thus obliged, when using nitrogen at 77° K., to confine oneself to a finally fairly low partial pressure (approximately 0.4). Nevertheless, it is possible to trace complete adsorption isotherms. For example, one can assume a position of 77° K. and employ a gas of which the vapor pressure at this temperature is low such as, for example, argon (vapour pressure at 77° K.=26 KPa). This introduces a considerable stress because the textural properties of the solids are in the majority of cases extracted from measurements based on nitrogen adsorption and it is fairly tricky to back up these measurements with those based on the use of other gases. This is linked to the fact that one knows only with considerable inaccuracy the surface area occupied by a molecule of gas (nitrogen, argon, krypton) and an offset of 10 to 20% between the nitrogen and argon measurements is normal (see, for example: "Adsorption, Surface Area and Porosity", S.J. Gregg and K.S.W. Sing, Academic Press Inc., second edition, 1982). Another method relates to mass control (U.S. Pat. No. 4,489,593). The range of flow rates necessary to establish a thermodynamic equilibrium being beyond the scope of conventional flow meters (flow rates generally less than 0.7 ml/min), it is therefore necessary to use flow meters which are especially adapted (U.S. Pat. No. 4,489,593) to the range: 0.05 to 0.7 ml/min. The apparatus constructed around these mass flow meters is complex and has recourse to a sophisticated electronics unit, so that the flow meters have to be supplied with an entirely constant pressure and placed in a thermostatically controlled enclosure. Indeed, a 1° C. fluctuation in the temperature of the gas introduced into the flow meters becomes translated into a fluctuation in rate of flow of about 1.5%, which is considerable. In practice, the apparatus described in U.S. Pat. No. 4,489,593 does not use a pure gas but a mixture for adsorption. Thus, for measurement of the isotherm of nitrogen adsorption at 77° K., a mixture of nitrogen and helium is used, which makes it necessary to use a reference ampoule so that the system is singularly complicated. One of the objects of the invention is to remedy the above-mentioned disadvantages.

Another object of the invention is to supply at any time and into the measuring circuit a substantially constant rate of gas flow such that the pressure of this gas in the measuring circuit containing the adsorbent sample is substantially in equilibrium.

SUMMARY OF THE INVENTION

It has been discovered that by not using mass flow regulators such as described in U.S. Pat. No. 4,489,593 nor sonic flow orifices or diaphragms, but regulated valves which are actuated by one or more programmable data generators, it is possible by regulating the pressure in a correctly calibrated reservoir circuit, to obtain rates of flow which are substantially constant and comprised between 0.025 and 25 ml/min measured under standard pressure and temperature conditions (20° C., 101325 Pa) advantageously comprised between 0.25 and 2 ml/min and preferably between 0.1 and 0.5 ml/min for pressures which are comprised between 10 KPa and 500 KPa and advantageously 30 KPa to 200 KPa, and preferably between 50 KPa and 150 KPa. The term 'substantially constant rate of flow' means that the fluctuations observed during recordings of the adsorption-desorption isotherms of a gas such as nitrogen for partial pressures comprised between 0 and 1 are generally less than 5% and are advantageously less than 2% and are preferably below 0.5%. In a practical way, to ensure a substantially constant rate of flow at adsorption, it is sufficient to charge the standard enclosure to a pressure above 80 KPa and preferably above 140 KPa, for example 150 KPa. To ensure a constant rate of flow at desorption, it should be ensured that the difference in pressure between the measuring circuit and the reservoir circuit is generally at least 200 Pa, being, for example, 250 Pa to $10^5$ Pa and preferably at least 1000 Pa, for example 1300 Pa to 2000 Pa.

The gas pressure in the measuring circuit is normally comprised between $1 \times 10^{-3}$ Pa and the saturation pressure of the gas at the temperature of liquid nitrogen and preferably between 0.1 Pa and the saturation pressure.

More precisely, the invention relates to a method of measuring the adsorption of a gas adsorbed by a solid sample comprising:

a) a stage involved in determining, at a substantially constant and clearly defined temperature, the volume of a reservoir circuit which has to contain the said gas and of a measuring circuit comprising a sample carrying enclosure, carried out in the presence of a gaseous medium which is not condensable at the temperature of the liquid nitrogen, b) a stage involving introduction of the sample which has been previously treated or which is in a suitable state of structure in the sample carrying enclosure, c) a stage involving determining the volume of the measuring circuit in the presence of the sample at a temperature which is substantially close to that of the liquid nitrogen, d) a stage involving the establishment of a vacuum in the reservoir circuit and in the measurement circuit containing the sample, at a pressure of approx. 1 Pa to $10^{-7}$ Pa, the method being characterised in that:

e) a known quantity of a gas which can be condensed at the temperature of liquid nitrogen is introduced into the reservoir circuit, f) a gas pressure drop is programmed in the reservoir circuit from 1 Pa to 7 KPa per minute by using a regulating valve $VP_1$ which has a preferably proportional aperture, in order to transfer a substantially constant rate of flow of gas towards the sample, a part of the said gas being adsorbed thereon until the saturation pressure of this gas is attained at the temperature of liquid nitrogen, the said rate of flow making it possible at any time to arrive at what is substantially a thermodynamic equilibrium, the pressure of the gas in the reservoir circuit being measured at intervals of time, g) at intervals in time, the pressure of the said gas on the sample in the measuring circuit is measured, h) by using suitable processing means, the isotherm of adsorption of the sample for the said gas is determined on a basis of the volume of the reservoir circuit (stage a), on a basis of the quantity of gas transferred from the reservoir circuit to the sample (stage e and f), on a basis of the gas pressure in the measuring circuit (stage g) and on a basis of the volume of the measuring circuit (stage c).

With the apparatus according to the invention it is possible to go beyond the limitations of the prior art. The complete measurement of adsorption-desorption isotherms is henceforth possible even with nitrogen at 77° K. without any need to report to sonic regulating systems or mass flow rate regulating systems featuring complex regulators.

By the term 'reservoir circuit' or 'reservoir part' one must understand the reservoir and the lines the volume of which is comprised between an isolating valve $V_1$, the pressure sensor $C_2$ and at least one regulating valve $VP_1$.

The term 'measuring circuit' is understood to mean the sample carrier and the lines connecting it to a regulated valve $VP_1$, the volume of which is comprised between the pressure sensor $C_1$, the isolating valves $V_4$ and $V_5$ and at least one regulating valve $VP_1$.

The term 'appropriate structure' is understood to imply a solid containing organic matter such as a sample of rock from which one does not extract this organic matter by pretreatment and on which after the sample has been fixed at 77° K. approx., the adsorption of gas and possibly the desorption of this gas are performed.

If necessary, measurement of the desorption of the gas adsorbed by the solid sample may be carried out, this being maintained at a temperature which is substantially close to that of liquid nitrogen. Generally, the following stages are then carried out:

1) the reservoir circuit is placed under a vacuum at a pressure of approx. 1 Pa to $10^{-7}$ Pa, the sample remaining at the saturation pressure of the gas adsorbed at the temperature of liquid nitrogen, 2) an increase in the gas pressure in the reservoir circuit of 1 Pa to 7 KPa per minute is programmed at least once by a regulated valve $VP_2$ or $VP_1$ in order to transfer a substantially constant rate of flow of gas adsorbed on the sample to the reservoir circuit until such time as the pressure in the measuring circuit is greater by at least 200 Pa than the pressure of the reservoir circuit, the said rate of flow of gas making it possible at any moment to be substantially in thermodynamic equilibrium at the level of the sample, the gas pressure in the reservoir circuit being measured at intervals of time, 3) at intervals of time, the gas pressure in the measuring circuit is measured, 4) by using suitable processing means, the isotherm of desorption of the sample for the said gas is determined on a basis of the volume of the reservoir circuit (stage a), the quantity of gas transferred from the sample to the reservoir circuit (stages 1 and 2), the pressure in the measuring circuit (stage 3) and the volume of the measuring circuit (stage a). The term 'regulated valve $VP_1$ or $VP_2$' must be understood to mean a regulated valve with either a proportional opening or adapted to open by pulses.

According to one characteristic feature of the method, the drop in gas pressure in the reservoir circuit during the adsorption phase and the rise in gas pressure in the reservoir circuit during the desorption phase are advantageously comprised between 10 Pa and 500 Pa·mn$^{-1}$ and preferably between 20 Pa to 200 Pa/min and even more preferably between 50 Pa and 150 Pa/min.

By multiplying in intervals of time ranging from 10 ms to several tens of seconds, measurements of pressures simultaneously in the reservoir circuit and in the measuring circuit, it is generally possible finely to describe the adsorption isotherm and hence if necessary the desorption isotherm. The volumes of the reservoir circuit and of the measuring circuit are entirely known, since a standard capacity, the volume of which has been determined by mercury, makes it possible to determine them. The dead space in the measuring circuit will preferably be measured at each test, the sample being in place and the sample carrier being immersed in a bath of liquid nitrogen at a substantially constant level which is maintained throughout the duration of the measurements.

The invention likewise relates to the apparatus for carrying out the method, during both the adsorption phase and during the desorption phase. It comprises:

a reservoir circuit (1);
a measuring circuit (2) comprising a sample carrier (3) and means (13) of maintaining the temperature at that of liquid nitrogen, connected to the sample carrier, the reservoir circuit and the measuring circuit being in a thermostatically controlled enclosure (50),
means (7) of establishing a vacuum and means of measuring the vacuum (31) in the reservoir circuit and the measuring circuit,
means (21, 22) for measuring and regulating the temperature of the reservoir circuit and of the measuring circuit in the said enclosure,
a supply (10) of gas which is not condensable at the temperature of liquid nitrogen connected to the reservoir circuit,
a supply (9) of gas which is condensable at the temperature of liquid nitrogen, connected to the measuring circuit.

The said apparatus is characterised in that it comprises in combination:

means of determining the volume of gas in the reservoir circuit comprising at least one pressure sensor $C_2$ adapted to measure the pressure of the gas contained in the reservoir circuit as a function of the time,
means of determining the volume of gas in the measuring circuit, comprising at least one pressure sensor $C_1$ adapted to measure the pressure of the gas in the measuring circuit as a function of the time,
at least one regulated valve, preferably of proportional opening ($Vp_1$) connecting the reservoir circuit to the measuring circuit,
means (40) for programming pressure connected to the pressure sensor $C_2$ adapted to control the regulated valve $Vp_1$, and
means of assessing and processing (14) data adapted to determine measurement of the adsorption of gas into sample and possibly measuring the desorption of gas from the sample, connected to pressure programming means (40), to means of determining the volumes of gas in the reservoir circuit, to means of determining the volume of gas in the measuring circuit and to means (13) of maintaining the temperature at that of liquid nitrogen in the measuring circuit and means (21, 22) of measuring and regulating the temperature of the reservoir circuit and the measuring circuit.

According to a characteristic feature of the apparatus, the pressure programming means generally comprise a microprocessor which delivers a signal which is directly proportional to the divergence between the measurement of the pressure at intervals in time from a desired value of the reservoir circuit pressure programmed as a function of the time, the said signal making it possible to control the regulated valve.

These intervals in time may be chosen advantageously to be constant.

BRIEF DESCRIPTION OF THE DRAWINGS

An example of embodiment of the apparatus according to the invention is shown by way of a schematic illustration in FIG. 1.

DETAILED DESCRIPTION OF THE DRAWINGS

Figure 1:
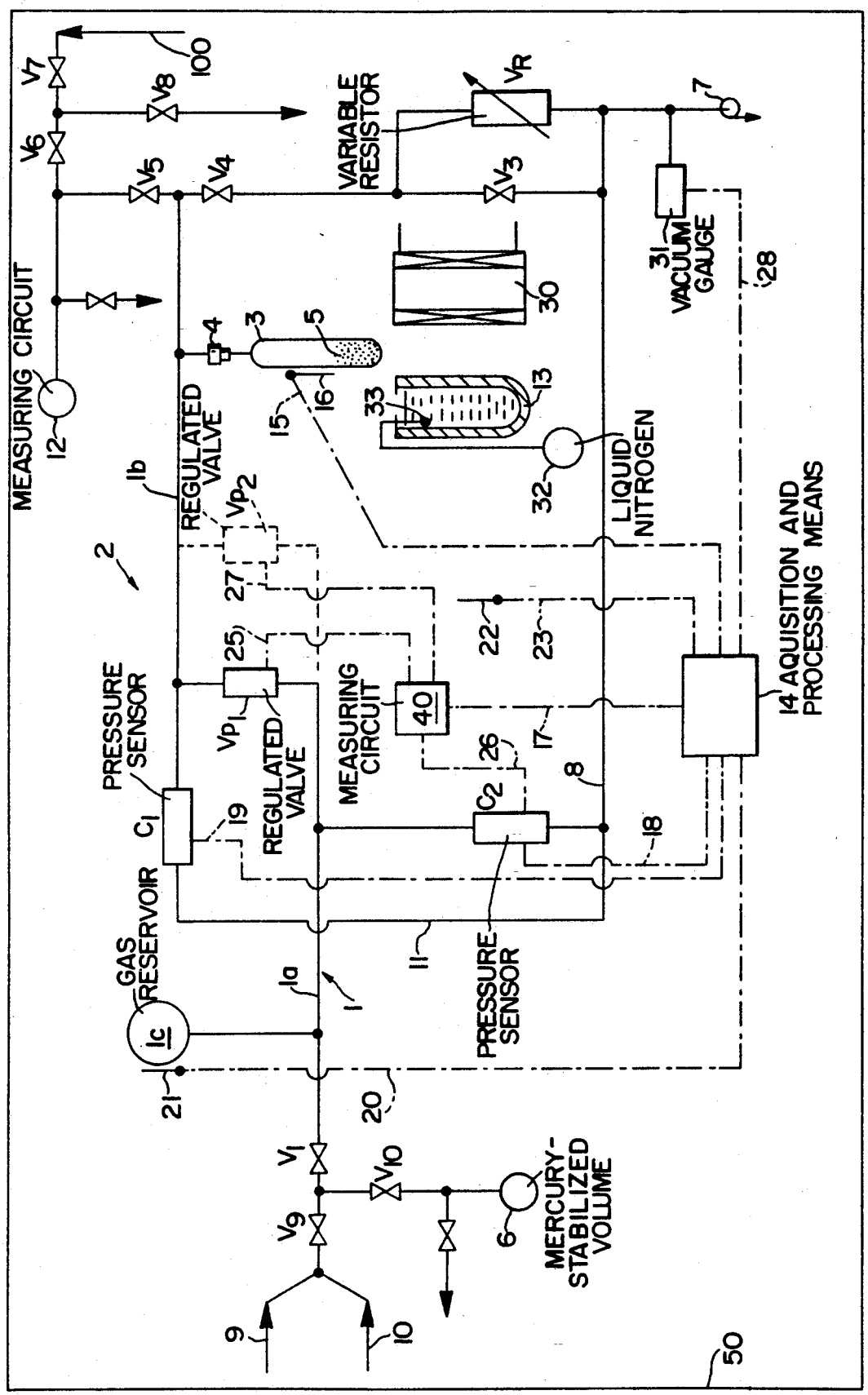

Before being pretreated, the solids or adsorbents have preferably been cleansed of organic matter, or decomposable acids or bases. Generally they are in the form of oxides and may contain in their structure water vapour, $CO_2$, air or adsorbed inert vapours. A regulated valve $V_R$ of regulable aperture makes it possible progressively to bring the sample carrier to a vacuum which is preferably close to 0.1 Pa to 0.01 Pa, and then by a valve $V_3$ to a vacuum level comprised between $10^{-3}$ and $10^{-5}$ Pa corresponding to that of the measurement which is taken by a vacuum gauge 31 on the basis of a turbomolecular pump 7 capable of a rate of flow of 50 l/s for nitrogen, for example.

Temperature pretreatment which is specific for a solid is carried out by an oven 30 equipped with a programmer (not shown).

According to an alternative form of pretreatment, this may be carried out by scavenging under an inert vector gas at a station suitably located outside the apparatus according to the invention.

The apparatus according to the invention comprises a reservoir circuit 1 comprising a gas reservoir 1c connected to a measuring circuit 2 containing a sample carrier 3 isolated by a sealing-tight valve 4. The sample carrier 3 contains a solid or adsorbent sample 5. A regulated enclosure 50 maintains the reservoir circuit and the measuring circuit at an appropriate and substantially constant temperature.

The volume of the reservoir circuit is perfectly well known and is determined once and for all when the apparatus is started up, thanks to a mercury-stabilised volume 6. It serves to store the gaseous nitrogen which will be transferred through lines 1a, 1b to the measuring circuit. At least one differential pressure sensor $C_2$ is associated with it ($5 \times 10^5$ Pa, full scale used for adsorption), connected to the line 1a and to the vacuum pump 7 through a line 8. A system of three stop valves $V_1$, $V_9$ and $V_{10}$ is connected to the reservoir circuit 1 and to the nitrogen 9 and helium 10 supplies and makes it possible to drain and fill this circuit with these gases at a desired pressure. The measuring circuit comprises at least one valve $VP_1$ for proportional opening (registered trade mark MKS model 248A, for example) which, subject to a desired pressure level, makes it possible to transfer through lines 1a and 1b the nitrogen from the reservoir circuit, passing it to the measuring circuit during the adsorption phase. During the desorption phase, the same valve may be used by a simple modification or, for reasons of convenience, it is possible to add to the circuit another valve $VP_2$ for proportional opening (the liaison shown by dotted lines in FIG. 1) for transfer of gas adsorbed on the sample to the reservoir circuit by lines 1b and 1a. These valves represent the principal element in conjunction with a programmed pressure control arrangement for co-operating in order to obtain a substantially constant rate of flow whatever the pressure may be. A differential pressure pick up $C_1$ ($10^5$ Pa, full scale) connected to the measuring circuit and to the vacuum pump 7 by lines 11 and 8 makes it possible at any moment to know the gas pressure in the measuring circuit.

Finally, via a valve $V_5$ there is attached to this measuring circuit a standard mercury-calibrated volume 12 and also a drain system comprising three valves $V_6$, $V_7$, $V_8$ which make it possible, from a helium supply 100, to introduce a known quantity of helium into the measuring circuit and to determine for each adsorbent its dead space under the conditions of measurement (the sample being immersed in liquid nitrogen in a cryogenic container 13 to the level which is respected during measurement).

A system for regulating the level of liquid nitrogen 32 maintains the level in the container 13 by means of a level sensor 33.

A programming system 40 connected to the valve $V_{p1}$, via a line 25 and to the differential pressure sensor $C_2$ by a line 26 makes it possible for control of the valve $V_{p1}$ to be subject to the drop in pressure in the reservoir circuit. This system 40 may also, through a dotted line 27, control the valve $V_{p2}$ used during desorption of the gas from the sample as a function of the pressure rise in the gas in the reservoir circuit, this rise being measured by the pressure sensor $C_2$ via the line 18.

Means 14 for alternating the whole of the apparatus for acquiring and processing data, are connected by a line 15 to a probe 16 for sensing the temperature of the sample carrier in the cryogenic container, via a line 17 to the programming system 40, by a line 18 to the pressure sensor $C_2$, by a line 19 to the pressure sensor $C_1$ and by a line 20 to a temperature sensor 21 disposed on the gas reservoir 1c. Finally, acquisition and processing means 14 receive data from a sensor 22 which ascertains the temperature in the regulated enclosure via a line 23 and from the vacuum gauge 31 via a line 28.

The apparatus functions in a thermostatically controlled enclosure the temperature of which is normally regulated at more or less 0.1° C. by appropriate means in order to carry out precise measurements of volumes and pressures.

The continuous adsorption or desorption measurements require apparatus for regulating the temperature so that it is substantially stable at the level of the sample. The divergence in temperature should generally be less than 0.5° C. and preferably less than 0.1° C. The level of liquid nitrogen in the cryogenic enclosure is generally regulated to within 0.3 mm and preferably to within 0.1 mm.

A measurement is usually carried in the following way:

Calibration of the Dead Space

Generally, this calibration is carried out with 99.9995% pure helium and makes it possible accurately to determine the free space surrounding the sample in the measuring circuit. This calibration is carried out automatically at the commencement of measurement by a computer which may be a multi-task microcomputer connected to a data acquisition unit. It consists of allowing helium into the standard volume at a desired pressure and in then allowing it to expand into the measuring circuit of the equipment, the sample being in place and the sample holder being immersed in the liquid nitrogen. Mariotte's law makes it possible to calculate the dead space.

Adsorption Measurement

With the entire measuring circuit of the apparatus under a vacuum but isolated from the vacuum source, nitrogen is transferred from the reservoir to the sample holder immersed in the liquid nitrogen, via the proportional valve $Vp_a$ which is programmed to provide a regular pressure drop to the level of the reservoir and therefore a substantially constant rate of flow of around 0.2 ml/min, for example. This rate of flow is generally such that thermodynamic equilibrium is attained at all times.

Desorption Measurement

When the saturation pressure of the gaseous nitrogen is attained above the sample, it is possible to proceed with desorption of the gas which has been adsorbed onto the sample.

When the reservoir circuit is empty, the proportional desorption valve $Vp_2$ makes it possible to carry out a reverse transfer of nitrogen from the measuring circuit to the reservoir circuit at a substantially constant rate of flow corresponding, for example to a programmed pressure increase of 100 Pa per minute in the reservoir circuit. As desorption is limited by equality of pressures between the two circuits of the apparatus, it is possible to proceed by stages of desorption. For example, at various intervals of time it is possible to stop the transfer of desorbed gas, empty the reservoir and possibly pursue the desorption stage until a gas pressure of around 200 Pa is attained in the measuring circuit.

During the course of adsorption and desorption, all the openings and closings of the valves are governed by the computer, which will likewise carry out logical tests to check the status of the system, the quality of the vacuum attained, and also the increase, decrease or stability of the pressure.

Figure 2:
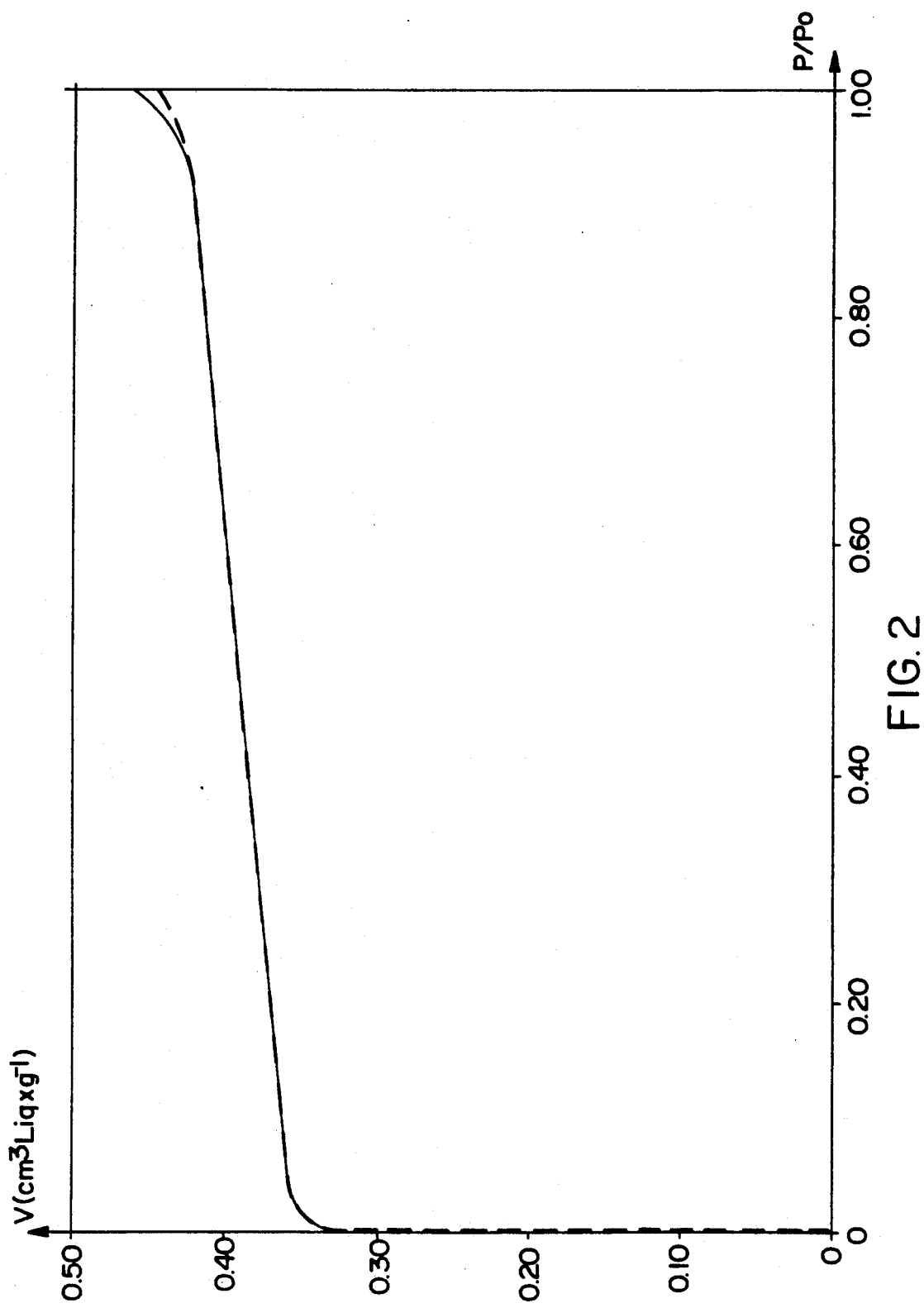
FIG. 2 is a graph of the adsorption-desorption curves.

All the calculations are carried out on the basis of acquisitions of pressure, temperature and time carried out and stored by a computer at a very high frequency (1 point per segment of 10 s). A table of the results and the adsorption-desorption curves are then published (FIG. 2).

Calculations of Quantities Absorbed

1. Adsorption

| | | |
|---|---|---|
| V = | volume of reservoir circuit | cm$^3$ |

| | -continued | |
|---|---|---|
| V1 = | dead volume of measuring circuit | cm³ |
| P = | pressure read at the level of the reservoir circuit | Pa |
| P' = | pressure read at the level of the measuring circuit | Pa |
| T = | time | mins |
| D = | rate of flow | cm³/min |
| V2 = | quantity of gaseous nitrogen transferred from the reservoir circuit to the measuring circuit as a function of the time T | cm³ |
| V3 = | quantity of gaseous nitrogen nedded to fill the measuring circuit | CM³ |
| t = | temperature in the thermostatically controlled enclosure | 0° c. |
| VA = | adsorbed volume of gas | cm³ |
| V'A = | adsorbed volume of liquid | cm³ |
| VV = | total volume introduced into adsorption at the partial pressure of 1 | cm³ |
| VD = | remaining volume adsorbed at the pressure P'n in question | cm³ |
| PO = | saturation pressure | Pa |
| Pp = | partial pressure. | |

On a basis of these parameters and of each of the values calculated, the rate of flow is determined and thus the volume at each partial pressure or as a function of the time.

$D = (((V \times P1 \times 293)/101325(273+t)) - ((V \times Pn \times 293/101325(273+t))/T$ P1 = starting pressure
Pn = pressure at P'/PO = 0.9

For each pressure acquired at the level of the sample (P'1, P'2, P'3 ... P'n):

$V2 = D \times T$
$V3 = (V1 \times P'n \times 293)/101325(273 \times t)$
$VA = V2 - V3$
$V'A = VA \times k$
$Pp = P'/PO$ in which k is the coefficient of conversion of gaseous nitrogen into liquid nitrogen and equal to 0.00155 under normal conditions (0° C., 101325 Pa) or equal to 0.00144 under standard conditions (20° C., 101325 Pa).

It is sufficient to trace a curve by showing as the ordinate the liquid adsorbed volumes V'A and on the abscissa the corresponding partial pressures to obtain the adsorption isotherm (FIG. 2, dotted graph).

2. Desorption
VV = total volume introduced into adsorption
$D = (V \times Pn \times 293)/101325 \times T(273+t)$
Pn = pressure at P/PO = 0.3
For each pressure acquired at the level of the sample (P'1, P'2, P'3 ... P'n, ... )
$V2 = D \times T$
$V3 = (V1 \times P' \times 293)/101325(273+t)$ The remaining quantity adsorbed $V_D$ is determined as a function of each partial pressure up to a partial pressure of nearly 0 in the measuring circuit.

$VD = VV - (V2 + V3)$
$Pp = P'/PO$

The isothermal desorption curve will be obtained by plotting on the ordinate the remaining adsorbed volumes and on the abscissa the corresponding partial pressures (FIG. 2, fine continuous line).

The most usual use of the apparatus according to the invention is the study of the texture of materials by physical adsorption, for example by the adsorption of nitrogen, argon or any other gas capable of serving to characterize the texture of solids (see, for example, "Adsorption, Surface Area and Porosity", S.J. Gregg and K.S.W. Sing, Academic Press Inc., second edition, 1982) at the temperature chosen, such as, for example, the temperature of liquid nitrogen for the adsorption of nitrogen, with the additional facility to describe the completely isothermal adsorption-desorption curve. All the phenomena of physisorption or chemisorption and also the kinetic study of reactions (isothermal or not) may be observed on this apparatus by adapting the range of the sensors and the volumes of the spaces to suit requirements.

The following example illustrates the invention without thereby restricting its scope.

EXAMPLE 1

It is proposed to use the apparatus according to the invention to measure the specific surface area BET, using nitrogen as the adsorbate (at a temperature of 77° K.), of a commercial NaY type zeolith: LZY52 (available from Union Carbide).

Pretreatment

A mass of about 150 mg of the NaY zeolith of which it is desired to measure the surface area is pretreated on the apparatus according to the invention, pursuing the following procedure: the sample is subjected to a vacuum at 20° C. until the extent of the vacuum is between $7.8 \times 10^{-3}$ Pa and $8 \times 10^{-4}$ Pa, the temperature of the sample is raised to 500° C. in successive stages:

from 20° C. to 100° C. at the rate of 2° C./min
a stage of 15 min at 100° C.
from 100° C. to 200° C. in stages of 2° C./min
a stage of 15 min at 200° C.
from 200° C. to 400° C. in stages of 5° C./min
a stage of 1 hour at 400° C.
from 400° C. to 500° C. in stages of 5° C./min
a stage of 12 hours at 500° C.

After having restored the temperature to 20° C., the sample of which the mass determined by weighing is equal to 0.1149 g, is transferred to the measuring circuit of the apparatus according to the invention.

Measurement

The temperature of the regulated enclosure is 21.5° C. The sample carrying cell is immersed in a reservoir filled with liquid nitrogen, the level of which is maintained constant by a regulating system, the measuring and reservoir circuits of the apparatus are placed under a vacuum (level of the vacuum between $1.3 \times 10^{-4}$ Pa and $1.3 \times 10^{-5}$ Pa). The volume of the reservoir circuit, determined beforehand, is 137.98 ml. The dead volume in the measuring circuit is determined with helium and is equal to 41.71 ml.

After determination of the dead volume, the sample is placed under a vacuum (value of $1.3 \times 10^{-4}$ Pa, the sample carrying cell still being at a temperature of 77° K. The initial pressure of the nitrogen in the reservoir is 171 KPa. The nitrogen is then transferred to the sample with a programmed pressure drop in the reservoir of 133 Pa/min corresponding to a mean rate of flow of 0.168 ml/min until such time as the partial pressure of nitrogen on the sample is substantially equal to 1. The adsorption isotherm is then obtained by virtue of the acquisition during this measurement phase of 887 pressure values from the reservoir circuit and the measuring circuit at intervals of 30 seconds (FIG. 2, dotted graph).

EXAMPLE 2

The sample of zeolith having absorbed an overall volume of liquid nitrogen of 0.448 ml/g or 289 ml/g of gaseous nitrogen (TPN) according to Example 1, the next step is to acquire the desorption isotherm. For this, the reservoir is placed under a vacuum and the nitrogen contained in the measuring circuit is expanded towards the reservoir with a programmed increase in pressure in the reservoir of 133.32 Pa/mn corresponding to a mean rate of flow of 0.179 ml/min. As soon as the difference between the pressure on the sample and the pressure on the reservoir circuit is equal to 666 Pa, acquisitions are stopped and the reservoir is placed under a vacuum before resuming the transfer of nitrogen. During the course of acquisition of the desorption isotherm, the operation previously described is repeated five times. As for the adsorption part, a high number of pressure values are recorded in order accurately to describe the desorption branch of the isotherm.

The isotherm for complete desorption of the zeolith studied is shown in FIG. 2 (fine line).

Via the data acquired and the foregoing equations, it has been determined that the surface area of the NaY zeolith studied, determined according to the conventional BET theory was 871 sq.m/g, the error on this value being estimated at more or less 2%.

By way of comparison, the BET surface area of the NaY zeolith, reference LZY52, indicated on the commercial pamphlet covering this product is 900 sq.m/g (BET one point).

We claim:

1. In a method of continuously measuring the adsorption of a gas adsorbed by a solid sample and comprising:
   (a) a stage involved in determining, at a substantially constant and clearly defined temperature, the volume of a reservoir circuit which has to contain the said gas and of a measuring circuit comprising a sample carrying enclosure, in the presence of a gaseous medium which is not condensable at the temperature of the liquid nitrogen;
   (b) a stage involving introduction of the sample which has been previously treated or which is in a suitable state of structure in the sample carrying enclosure;
   (c) a stage involving determining the volume of the measuring circuit in the presence of the sample at a temperature which is substantially close to that of the liquid nitrogen; and
   (d) a stage involving the establishment of a vacuum in the reservoir circuit and in the measurement circuit containing the sample, at a pressure of approx. 1 Pa to $10^{-7}$ Pa, the improvement comprising:
   (e) a known quantity of the gas which can be condensed at the temperature of liquid nitrogen is introduced into the reservoir circuit;
   (f) programming a controller to maintain a gas pressure drop in the reservoir circuit from 1 Pa to 7 KPa per minute by using a regulating valve $VP_1$, and passing gas continuously through said regulating valve in order to transfer a substantially constant rate of flow of gas towards the sample, a part of the said gas being adsorbed thereon until the saturation pressure of this gas is attained at the temperature of liquid nitrogen, the said rate of flow, enabling a substantially thermodynamic equilibrium to be attained at all times;
   (g) at intervals in time, the pressure of the gas in the reservoir circuit is measured, and the pressure of the said gas on the sample in the measuring circuit is measured; and
   (h) by using suitable processing means, the isotherm of adsorption of the sample for the said gas is determined on a basis of the volume of the reservoir circuit (stage a), on a basis of the quantity of gas transferred from the reservoir circuit to the sample (stage e and f), on a basis of the gas pressure in the measuring circuit (stage g) and on a basis of the volume of the measuring circuit (stage c).

2. A method according to claim 1, in which the gas which is condensable at the temperature of liquid nitrogen is chosen from the group consisting of nitrogen, argon, krypton and xenon and preferably nitrogen.

3. A method according to claim 1, in which a pressure drop in the condensable gas in the reservoir circuit is programmed for the adsorption phase while an increase in pressure of the condensable gas is programmed for the desorption phase in the reservoir circuit, of 50 Pa to 150 Pa/min.

4. A method according to claim 1, further comprising determining from resultant isotherms at least one surface function of the solid sample.

5. A method according to claim 1, in which the sample adsorbs as volume of gas corresponding to a rate of flow of 0.025 to 25 ml per second under standard temperature and pressure conditions.

6. A method according to claim 5, wherein the rate of flow is 0.1 to 0.5 ml/sec.

7. A method according to claim 1, in which during the adsorption phase, the pressure in the reservoir circuit is 10 KPa to 500 KPa and the pressure in the measuring circuit is comprised between $1 \times 10^{-3}$ Pa and the saturation pressure of the gas at the temperature of the liquid nitrogen.

8. A method according to claim 7, wherein the pressure in the reservoir circuit is 50 to 150 KPa.

9. A method according to claim 1, further comprising determining from resultant isotherms at least one textural property of the solid.

10. A method according to claim 9, wherein the textural property is the specific surface area.

11. A method of continuously measuring desorption of the gas adsorbed by the solid sample, according to claim 1, the sample being at a temperature which is substantially close to that of liquid nitrogen, wherein:
   (1) the reservoir circuit is placed under a vacuum at a pressure of approx. 1 Pa to $10^{-7}$ Pa, the sample remaining at the saturation pressure of the gas adsorbed at the temperature of liquid nitrogen;
   (2) programming a controller at least once to maintain an increase in the gas pressure in the reservoir circuit of 1 Pa to 7 KPa per minute by a regulated valve $VP_2$ or $VP_1$, and gas is passed continuously through said regulating valve in order to transfer a substantially constant rate of flow of gas adsorbed on the sample to the reservoir circuit until such time as the pressure in the measuring circuit is greater by at least 200 Pa than the pressure of the reservoir circuit, the said rate of flow of gas, enabling a substantially thermodynamic equilibrium to be attained at all times at the level of the sample;
   (3) at intervals of time, the gas pressure in the reservoir circuit is measured, and the gas pressure in the measuring circuit is measured; and (4) by using suitable processing means, the isotherm of desorption of the sample for the said gas is determined on a basis of the volume of the reservoir circuit (stage a), the quantity of gas transferred from the sample to the reservoir circuit (stages 1 and 2), the pressure in the measuring circuit (stage 3) and the volume of the measuring circuit (stage a, claim 1).

12. A method according to claim 11, in which the difference in pressure between the measuring circuit and the reservoir circuit during the desorption phase is at least 200 Pa.

13. A method according to claim 12, wherein the difference in pressure is at least 1000 Pa.

14. In an apparatus for determining the measurement of adsorption or measurement of desorption of a gas adsorbed by a solid sample comprising in combination:
 a reservoir circuit (1),
 a measuring circuit (2) comprising a sample carrier (3) and means (13) of maintaining the temperature at that of liquid nitrogen connected to the sample carrier, the reservoir circuit and measuring circuit being in a thermostatically controlled enclosure (50),
 means (7) of establishing a vacuum and means of measuring the vacuum (31) in the reservoir circuit and the measuring circuit,
 means (21, 22) of measuring and regulating the temperature of the reservoir circuit and of the measuring circuit in the said enclosure,
 a supply (10) of gaseous medium which cannot be condensed at the temperature of liquid nitrogen, connected to the reservoir circuit,
 a supply (9) of gas which is condensable at the temperature of liquid nitrogen, connected to the measuring circuit, the improvement comprising in combination:
 means of determining the volume of gas in the reservoir circuit comprising at lest one pressure sensor $C_2$ adapted to measure the pressure of the gas in the reservoir circuit as a function of the time,
 means of determining the volume of gas in the measuring circuit comprising at least one pressure sensor $C_1$ adapted to measure the pressure of the gas in the measuring circuit as a function of the time,
 at least one regulating valve ($VP_1$) connecting the reservoir circuit to the measuring circuit said regulating valve having a proportional opening,
 programmable pressure controller means (40), connected to the pressure sensor $C_2$ adapted to control the regulating valve $VP_1$ so as to permit a continuous substantially constant rate of flow, and
 means of acquisition and processing (14) of data adapted to determine the measurement of the adsorption of gas in the sample and measurement of the desorption of the gas from the sample connected to the pressure controller means (40), to the means of determining the volumes of gas in the reservoir circuit, the means of determining the volume of gas in the measuring circuit, the means (13) of maintaining the temperature at that of liquid nitrogen in the measuring circuit and means (21, 22) of measuring and regulating the temperature of the reservoir circuit and of the measuring circuit.

15. An apparatus according to claim 14, comprising means of pretreatment in a regulated vacuum (VR) and for programming temperature in furnace (30), connected to the measuring circuit, to the means of establishing a vacuum and of measuring the vacuum and to the means for the acquisition and processing of the data.

16. An apparatus according to claim 14, wherein the programmable pressure controller means (40) comprises a microprocessor delivering a signal which is directly of the pressure at intervals of time and a reference value of the pressure of the reservoir circuit programmed as a function of the time, the said signal permitting control of the regulating valve.

17. An apparatus according to claim 14, comprising at least one space (6) connected to the said condensable gas supply and to the said supply of non-condensable gas.

18. An apparatus according to claim 14, wherein the means of maintaining temperature at that of liquid nitrogen connected to the measuring circuit comprise a liquid nitrogen supply connected to a regulator of liquid nitrogen level in a cryogenic container (13).

19. An apparatus according to claim 14, comprising at least one isolating valve V4 situated between the measuring circuit and the means of establishing the vacuum.

20. An apparatus according to claim 14, in which the regulating valve is a valve for proportional opening.

* * * * *